United States Patent
Gaze

(10) Patent No.: US 9,182,413 B2
(45) Date of Patent: Nov. 10, 2015

(54) METHODS AND DEVICES FOR DIAGNOSING CARDIAC DISORDERS

(75) Inventor: David Gaze, London (GB)

(73) Assignee: ST. GEORGE'S HEALTHCARE NHS TRUST, London (GB)

( * ) Notice: Subject to any disclaimer, the term of this patent is extended or adjusted under 35 U.S.C. 154(b) by 0 days.

(21) Appl. No.: 13/574,035

(22) PCT Filed: Jan. 21, 2011

(86) PCT No.: PCT/GB2011/000073
§ 371 (c)(1),
(2), (4) Date: Sep. 18, 2012

(87) PCT Pub. No.: WO2011/089392
PCT Pub. Date: Jul. 28, 2011

(65) Prior Publication Data
US 2013/0115633 A1     May 9, 2013

(30) Foreign Application Priority Data
Jan. 22, 2010   (GB) .................................. 1001073.4

(51) Int. Cl.
*G01N 33/53*     (2006.01)
*G01N 33/68*     (2006.01)
*G01N 33/50*     (2006.01)

(52) U.S. Cl.
CPC ........ *G01N 33/6893* (2013.01); *G01N 33/5088* (2013.01); *G01N 33/5302* (2013.01); *G01N 33/6872* (2013.01); *G01N 33/6887* (2013.01); *G01N 2800/32* (2013.01); *G01N 2800/324* (2013.01); *G01N 2800/52* (2013.01)

(58) Field of Classification Search
CPC ............ C12N 5/0657; G01N 2800/52; G01N 2800/32; G01N 2800/324; G01N 33/53; G01N 33/5002; A61K 38/45; C07K 14/47
See application file for complete search history.

(56) References Cited

U.S. PATENT DOCUMENTS

2003/0104393 A1 * 6/2003 Sharp et al. ....................... 435/6

FOREIGN PATENT DOCUMENTS

EP           1913949       * 4/2008    ............. A61K 33/36

OTHER PUBLICATIONS (Sun et al., Circulation, 1994; vol. 89 pp. 793-798.*
Murphy et al., Heart Fail Rev 2007; vol. 12:293-300.*
Armoni et al., (J. Biol. Chem. 2005, 280:34786-34795).*
Li et al., (Journal of Pharmacological and Toxicological Methods 43;2000, p. 85-90).*
Szablewski et al., Glucose transporters in diabetic patients 2007,7,4,204-212.*
Scheepers et al., (Journal of Parenteral and Enteral Nutrition, 2004;p. 364-371).*
Collinson et al., "Biomarkers of Cardiovascular Damage", Med Princ Pract, 2007, 16: 247-261.
Davies et al., "Intramyocardial platelet aggregation in patients with unstable angina suffering sudden ischemic cardiac death", Circulation, 1986, 73: 418-427.
Doehner et al., "Impaired Insulin Sensitivity as an Independent Risk Factor for Mortality in Patients with Stable Chronic Heart Failure", Journal of American College of Cardiology, 2005, vol. 46, No. 6, 1019-1026.
Doehner et al., "Reduced glucose transporter GLUT4 in skeletal muscle predicts insulin resistance in non-diabetic chronic heart failure patients independently of body composition", International Journal of Cardiology, 2010, 138:19-24.
Falk et al., "Unstable angina with fatal outcome: dynamic coronary thrombosis leading to infarction and/or sudden death", Circulation, 1985, vol. 71, No. 4, 699-708.
Gaze , "Sensitive Cardiac Troponin Assays: Myth and Magic or a Practical Way Forward?", J Med Biochem, 2010, 29: 269-273.
Keller et al., "Sensitive Troponin I Assay in Early Diagnosis of Acute Myocardial Infarction", N Engl J Med, 2009, 361: 868-77.
Reichlin et al., "Early Diagnosis of Myocardial Infarction with Sensitive Cardiac Troponin Assays", N Engl J Med, 2009, 361: 858-67.
Shave et al., "The Influence of Exercise Upon Cardiac Biomarkers: A Practical Guide for Clinicians and Scientists", Current Medicinal Chemistry, 2007, 14: 1427-1436.
Thygesen et al., "Universal Definition of Myocardial Infarction", Circulation, 2007, 116: 2634-53.
Adams et al., "Cardiac Tropinin I. A Marker With High Specificity for Cardiac Injury", Circulation, 1993; 88:101-106.
European Application No. EP11701541.2, Examination Report dated Oct. 10, 2014.
La Vecchia et al., "Cardiac Troponin I as Diagnostic and Prognostic Marker in Severe Heart Failure", The Journal of Heart and Lunch Transplatation, 2000, 19(7):644-652.
Okazaki et al., "Autoantibodies Against Cardiac Troponin I Are Responsible for Dilated Cardiomyopathy in PD-1-Deficient Mice", Nature Medicine, 2003, 9(2):1477-1483.

* cited by examiner

*Primary Examiner* — Shafiqul Haq
*Assistant Examiner* — Carmencita M Belei
(74) *Attorney, Agent, or Firm* — Kilpatrick Townsend & Stockton LLP

(57) ABSTRACT

A method for diagnosing a cardiac disorder by detecting levels of cardiac-specific membrane polypeptides in tissue samples.

6 Claims, 5 Drawing Sheets

SEQUENCE LISTING

<160> NUMBER OF SEQ ID NOS: 1

<210> SEQ ID NO 1
<211> LENGTH: 509
<212> TYPE: PRT
<213> ORGANISM: Homo sapiens

<400> SEQUENCE: 1

```
Met Pro Ser Gly Phe Gln Gln Ile Gly Ser Glu Asp Gly Glu Pro Pro
1               5                   10                  15

Gln Gln Arg Val Thr Gly Thr Leu Val Leu Ala Val Phe Ser Ala Val
                20                  25                  30

Leu Gly Ser Leu Gln Phe Gly Tyr Asn Ile Gly Val Ile Asn Ala Pro
            35                  40                  45

Gln Lys Val Ile Glu Gln Ser Tyr Asn Glu Thr Trp Leu Gly Arg Gln
        50                  55                  60

Gly Pro Glu Gly Pro Ser Ser Ile Pro Pro Gly Thr Leu Thr Thr Leu
65                  70                  75                  80

Trp Ala Leu Ser Val Ala Ile Phe Ser Val Gly Gly Met Ile Ser Ser
                85                  90                  95

Phe Leu Ile Gly Ile Ile Ser Gln Trp Leu Gly Arg Lys Arg Ala Met
                100                 105                 110

Leu Val Asn Asn Val Leu Ala Val Leu Gly Gly Ser Leu Met Gly Leu
            115                 120                 125

Ala Asn Ala Ala Ala Ser Tyr Glu Met Leu Ile Leu Gly Arg Phe Leu
        130                 135                 140

Ile Gly Ala Tyr Ser Gly Leu Thr Ser Gly Leu Val Pro Met Tyr Val
145                 150                 155                 160

Gly Glu Ile Ala Pro Thr His Leu Arg Gly Ala Leu Gly Thr Leu Asn
                165                 170                 175

Gln Leu Ala Ile Val Ile Gly Ile Leu Ile Ala Gln Val Leu Gly Leu
            180                 185                 190

Glu Ser Leu Leu Gly Thr Ala Ser Leu Trp Pro Leu Leu Leu Gly Leu
        195                 200                 205

Thr Val Leu Pro Ala Leu Leu Gln Leu Val Leu Leu Pro Phe Cys Pro
210                 215                 220

Glu Ser Pro Arg Tyr Leu Tyr Ile Ile Gln Asn Leu Glu Gly Pro Ala
225                 230                 235                 240

Arg Lys Ser Leu Lys Arg Leu Thr Gly Trp Ala Asp Val Ser Gly Val
                245                 250                 255

Leu Ala Glu Leu Lys Asp Glu Lys Arg Lys Leu Glu Arg Glu Arg Pro
            260                 265                 270

Leu Ser Leu Leu Gln Leu Leu Gly Ser Arg Thr His Arg Gln Pro Leu
        275                 280                 285

Ile Ile Ala Val Val Leu Gln Leu Ser Gln Gln Leu Ser Gly Ile Asn
        290                 295                 300

Ala Val Phe Tyr Tyr Ser Thr Ser Ile Phe Glu Thr Ala Gly Val Gly
305                 310                 315                 320

Gln Pro Ala Tyr Ala Thr Ile Gly Ala Gly Val Val Asn Thr Val Phe
                325                 330                 335

Thr Leu Val Ser Val Leu Val Glu Arg Ala Gly Arg Arg Thr Leu
            340                 345                 350

His Leu Leu Gly Leu Ala Gly Met Cys Gly Cys Ala Ile Leu Met Thr
        355                 360                 365
```

-continued

```
Val Ala Leu Leu Leu Leu Glu Arg Val Pro Ala Met Ser Tyr Val Ser
    370                 375             380

Ile Val Ala Ile Phe Gly Phe Val Ala Phe Phe Glu Ile Gly Pro Gly
385                 390             395                 400

Pro Ile Pro Trp Phe Ile Val Ala Glu Leu Phe Ser Gln Gly Pro Arg
            405             410                 415

Pro Ala Ala Met Ala Val Ala Gly Phe Ser Asn Trp Thr Ser Asn Phe
            420             425             430

Ile Ile Gly Met Gly Phe Gln Tyr Val Ala Glu Ala Met Gly Pro Tyr
        435             440             445

Val Phe Leu Leu Phe Ala Val Leu Leu Leu Gly Phe Phe Ile Phe Thr
    450             455             460

Phe Leu Arg Val Pro Glu Thr Arg Gly Arg Thr Phe Asp Gln Ile Ser
465             470             475             480

Ala Ala Phe His Arg Thr Pro Ser Leu Leu Glu Gln Glu Val Lys Pro
            485             490             495

Ser Thr Glu Leu Glu Tyr Leu Gly Pro Asp Glu Asn Asp
        500             505
```

METHODS AND DEVICES FOR DIAGNOSING CARDIAC DISORDERS

PRIOR RELATED APPLICATIONS

This application is a national stage application of PCT/GB2011/000073, filed on Jan. 21, 2011, which claims priority to GB 1001073, filed on Jan. 22, 2010, each of which is incorporated herein by reference in its entirety.

TECHNICAL FIELD

This invention is in the field of cardiology. In particular the invention relates to methods and devices for diagnosing cardiac disorders.

BACKGROUND ART

Heart disease and cardiac disorders are a major cause of death in the developed world. One particular category is described as acute cardiac disorders (ACD). ACDs are caused by the rupture or erosion of atheromatous plaques in epicardial coronary arteries. The exposure of the plaque core activates the clotting cascade and results in thrombosis within the plaque. This then initiates platelet aggregation. There are three possible mechanisms by which damage to the myocardium may then occur.

Firstly, intraluminal platelet aggregation may cause sufficient vascular occlusion for cardiomyocyte damage to occur. Occlusion does not have to be total to produce myonecrosis. Partial occlusion will produce a reduction in the rate of blood supply in the myocardium downstream. If there is already supply/demand mismatch in this area, the reduction in blood supply may be enough to render an area of myocardium non-viable. The tissue will then become sufficiently ischaemic for necrosis to occur. This is most likely to affect small areas of myocardium at the watersheds of different branches of the vascular supply.

The second mechanism is the release of platelet microaggregates. These will embolise small vessels causing ischaemia and localised infarction (Davies et al, 1986; Falk E, 1995).

Finally, progression of white thrombus formation to activation of the clotting cascade will result in partial or total occlusion of the vessel. Partial occlusion will produce ischaemia and necrosis if it produces inadequate flow to maintain tissue viability downstream, as described above. Total occlusion will initially produce ischaemia. This will progress to necrosis if maintained and there is inadequate or no collateral blood supply.

In order to either limit or prevent myocardial damage it is therefore desirable to detect ischaemia caused by cardiac disorders before it progresses to necrosis/infarction. In theory, if ischaemia can be detected prior to progression to necrosis, it may be possible to intervene to either limit or prevent myocardial damage.

Attempts have been made to detect ischemia using a number of biomarkers, for example choline, unbound free fatty acids (FFAu) and ischemia-modified albumin (IMA®). Unfortunately all of these markers suffer from the disadvantage that assays relying on them can not easily discriminate between patients with or without cardiac disorders. In addition, although these assays may be sensitive, allowing early detection, they lack specificity. Furthermore, the markers are often chemically derived and are produced in any ischemia or as part of normal physiology, for example lactate or free fatty acids. Other early markers such as myoglobin and CK-MB isoenzyme are elevated in non-cardiac diseases such as skeletal muscle trauma/diseases and renal failure.

In light of the problems associated with ischemia biomarkers, tests for biomarkers of myocardial necrosis are used to diagnose cardiac disorders. The measurement of the cardiac troponins, cardiac troponin T (cTnT) and cardiac troponin I (cTnI), have become recognised as the diagnostic reference standard for myocardial necrosis and as such may be predictive for myocardial infarction. Release kinetics show troponin elevation occurs approximately 4-6 hours after the onset of the myocardial necrosis and peak at 12-14 hours. There is therefore a window of 4-6 hours in which myocardial damage is occurring, but a diagnosis cannot be made and the correct treatment cannot be initiated.

In addition, the sensitive nature of these tests has also revealed that myocardial necrosis is also found in a range of other clinical situations, highlighting the need to use all clinical information for diagnosis of cardiac disorders.

There is therefore a need in the art for methods which are capable of sensitively, specifically and rapidly detecting the onset of cardiac ischemia and myocardial necrosis caused by cardiac disorders at the earliest possible point.

DISCLOSURE OF THE INVENTION

The inventor has surprisingly realised that cardiac specific membrane polypeptides can be used to overcome the problems associated with the prior art and provide novel biomarkers for use in methods which are capable of sensitively, specifically and rapidly detecting the onset of cardiac ischemia and myocardial necrosis.

Accordingly, the invention provides a method of diagnosing a cardiac disorder in a patient, comprising detecting the level of a cardiac specific membrane polypeptide in a patient sample and comparing said level to a control level, wherein a level that is higher to said control level is indicative of the disorder. Preferably the cardiac disorder is an acute cardiac disorder (ACD).

Acute cardiac disorders begin with ischemia. If ischemia is not resolved, a complex pathway of events leads to the disruption of the plasma membrane, which in turn leads to the release of the cellular contents into the surrounding environment and eventually into the bloodstream.

The troponin assays known in the art rely on the release of the cellular contents in order to be able to detect cTnT and/or cTnI. However, both cTnT and cTnI are intracellular polypeptides and the vast majority (>90%) of these molecules are bound to the myofibril contractile apparatus within the cell. Once the plasma membrane has been disrupted there is a lag period, in which the contractile apparatus is disrupted, the troponins released and migration through the cytoplasm into the surrounding environment and eventually the circulation occurs. This lag period is the reason that troponin levels are not elevated until 4-6 hours after the onset of the myocardial infarction. More sensitive assays are being developed to detect troponin earlier in clinical samples.

The use of cardiac specific membrane polypeptides as biomarkers for ischemia overcomes this problem. Unlike the troponins, the release of cardiac specific membrane polypeptides does not require necrosis or the complete disruption of the plasma membrane to occur. Ischemia causes permeability changes in the cellular membranes, causing them to become 'fluid' and disjointed. Therefore the loss of cardiac specific membrane polypeptides can occur without the cell becoming necrotic allowing for earlier detection.

Once necrosis occurs, additional cardiac specific membrane polypeptides are released almost immediately into the surrounding environment and are readily detectable in the patient's blood stream. Therefore the 4-6 hour lag period observed with troponin assays is avoided and correct diagnosis and therapeutic intervention can be made at an earlier stage, increasing the likelihood that myocardial damage is reduced or prevented and earlier treatment given.

Necrosis does not have to occur to release membrane integral polypeptides. In ischemia permeability changes occur and the membranes become 'fluid' and disjointed. Loss of membrane polypeptides can occur without the cell becoming necrotic.

In a preferred embodiment the cardiac specific membrane polypeptide used as a biomarker for ischemia is glucose transporter isoform 4 (Glut4). Glut4 is a bound transporter polypeptide found on the cell surface membrane. In addition to conferring the advantages described above for membrane polypeptides, the use of Glut4 as a biomarker confers an additional advantage.

During periods of myocardial ischemia, cardiomyocytes have to rely solely on anaerobic glycolysis for energy production; for this, the cells have to depend on increased glucose entry inside the cell as well as increased glycolysis. This is achieved by the stimulation of α1-adrenoreceptors which increases glucose transport inside the cardiomyocytes by translocating glucose transporter Glut4 from the cytoplasm to the plasma membrane. Therefore, there is a higher concentration of Glut4 in the plasma membranes of cells under ischemic conditions.

As there is a higher concentration of Glut4 in the plasma membrane of cells under ischemic conditions, disruption of these cells will release a larger amount of Glut4 in to the patient's bloodstream when compared to cardiac cellular disruption caused by normal cell death. This contrast allows for more sensitive detection of Glut4 and therefore cardiac ischemia and necrosis.

Preferably the cardiac disorder is characterised by cellular damage of cardiac tissue. Such diseases include, but are not limited to: hypertension, angina, ischemia, myocardial infarction, cardiorenal disease and reperfusion injury.

Preferably the patient sample is a blood sample.

Preferably the level of the cardiac specific membrane polypeptide is assessed by contacting a patient sample with a detection reagent which binds specifically to the cardiac specific membrane polypeptide. Preferably the detection reagent is an antibody.

The invention also includes a method for evaluating the effectiveness of a treatment for a heart disorder, comprising detecting the level of cardiac specific membrane polypeptide in a patient sample before, during and/or after treatment and comparing said level to a control level.

The invention also includes a diagnostic device for use in diagnosing a cardiac disorder, wherein the device permits determination of the level of a cardiac specific membrane polypeptide in a patient sample and comparison of said level to a control level, wherein a level that is higher to said control level is indicative of the disorder. Preferably the cardiac disorder is an ACD.

Preferably the diagnostic device comprises a detection reagent which binds specifically to the cardiac specific membrane polypeptide.

The invention also includes a cardiac specific membrane protein for use in a method of diagnosing a cardiac disorder in a patient, the method comprising detecting the level of a cardiac specific membrane polypeptide in a patient sample and comparing said level to a control level, wherein a level that is higher to said control level is indicative of the disorder. Preferably the disorder is an ACD.

Preferably the cardiac specific membrane polypeptide is Glut4.

A Method of Diagnosing

The invention provides a method for diagnosing a cardiac disorder. It will be appreciated that "diagnosis" according to the invention can range from a definite clinical diagnosis of a disorder to an indication that the patient should undergo further testing which may lead to a definite diagnosis. For example, the method of the invention can be used in combination with other methods for diagnosing cardiac disorders, for example physical assessment of a patient's symptoms, including electrocardiograms (ECG), as well as other biochemical assays, for example assessment of troponin levels.

Furthermore, it will be appreciated that "diagnosis" according to the invention can indicate that a patient is at risk of suffering from a cardiac disorder and therefore requires further monitoring, either using the methods of the invention or with other methods for diagnosing cardiac disorder. For example, a patient may show a higher level of a cardiac specific membrane protein when compared to a control. However this level may be only marginally higher and thus the patient may require further monitoring to determine whether the level is changing. In this situation the methods provide a means of risk assessment for a patient.

Furthermore, diagnosis includes monitoring the progress of a cardiac disorder in a patient already suspected or known to have a cardiac disorder. In addition, diagnosis includes providing a prognostic indication for patients who are known to have a cardiac disorder. For example, different levels of a cardiac specific membrane protein may indicate different clinical outcome for a patient.

The efficacy of a treatment regimen for the treatment of cardiac disorders can also monitored by the methods of the invention e.g. to determine its efficacy.

All of these techniques fall within the general meaning of "diagnosis" in the present invention.

Cardiac Disorder

As described above, the invention is based on the surprising discovery that cardiac specific membrane polypeptides are rapidly released into the patient's circulation following disruption of the plasma membrane. Therefore, the methods of the invention are suitable for detecting any type of cardiac disorder in which cardiac cellular damage occurs. Therefore, the term "cardiac disorder" as used herein refers to any disease or disorder of the heart which cellular damage occurs. Preferably the cardiac disorder is an acute cardiac disorder.

Preferably the disorder is selected from the group consisting of hypertension, angina, ischemia, myocardial infarction and reperfusion injury.

Cardiac Specific Membrane Polypeptide

The term "cardiac specific membrane polypeptide" refers to any polypeptide which is attached to or associated with the membrane of a cardiac cell. Preferably the polypeptide will be specific to cardiac cells, i.e. of the polypeptide present in the patient's body greater than 80% will be found in cardiac cells, i.e. at least 81, 82, 83, 84, 85, 86, 87, 88, 89, 90, 91, 92, 93 94, 95, 96, 97, 98, 99, 99.5, 99.5% or more.

Cardiac specific membrane polypeptides include integral and peripheral membrane polypeptides. Preferably the cardiac specific membrane polypeptide is Glut4.

The methods of the invention also include measuring more than one cardiac specific membrane protein. For example, the level of two or more cardiac specific membrane proteins can be measured in a patient sample. Therefore the term "cardiac specific membrane protein" as used herein also includes the plural, i.e. two or more cardiac specific membrane proteins.

Glut4

As described above, Glut4 is a bound transporter polypeptide found on the cell surface membrane of cardiac cells. Glut4 is an insulin-regulated glucose transporter. In the absence of insulin, Glut4 is sequestered in the interior of the cell within lipid bilayers of vesicles. Insulin induces the translocation of Glut4 from intracellular storage sites to the plasma membrane. The presence of insulin stimulates Glut4 to be expressed on the plasma membrane.

Glut4 is also expressed on the cell membrane during periods of myocardial ischemia. During such periods cardiomyocytes have to rely solely on anaerobic glycolysis for energy production; for this, the cells have to depend on increased glucose entry inside the cell as well as increased glycolysis. This is achieved by the stimulation of a1-adrenoreceptors which increases glucose transport inside the cardiomyocytes by translocating glucose transporter Glut4 from the cytoplasm to the plasma membrane.

At the cell surface, Glut4 facilitates the diffusion of circulating glucose down its concentration gradient into the cells.

Glut4 (also known as SLC2A4) is a polypeptide of 509 amino acids described under NCBI accession number NP_001033 and given herein as SEQ ID NO:1. Glut4 maps at chromosome 17: 7.13-7.13 Mb.

The term "Glut4" refers to the full length polypeptide as described above as well as fragments and variants of the polypeptide which result from normal degradation of the polypeptide within the body and from the normal genetic diversity across a population.

For example, once Glut4 is released from the cellular membrane it may be exposed to proteases within the body which cause its degradation. The term "Glut4" also includes (a) a polypeptide comprising a fragment of at least aa amino acids of a Glut4 polypeptide and (b) a polypeptide comprising an amino acid sequence having at least bb % identity to a Glut4 polypeptide. These polypeptides include variants (e.g. allelic variants, homologs, orthologs, mutants, etc.).

The percentage value of bb as used above may be 50, 60, 65, 70, 75, 80, 85, 90, 91, 92, 93, 94, 95, 96, 97, 98, 99, 99.5, 99.9 or 100.

The value of aa as used above may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 60, 70, 75, 80, 90, 100, 110, 120, 130, 140, 150, 200, 250, 300, 350, 400 or more. The value of aa may be less than 509 (e.g. less than 500, 250 or 50).

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of "Current Protocols in Molecular Biology". A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in Smith & Waterman (1981).

Patient Sample

Where the methods of the invention are based on detecting polypeptide molecules, the patient sample is preferably a tissue sample, preferably, a blood sample. Other possible sources of patient samples include isolated cells, whole tissues, or bodily fluids (e.g. blood, plasma, serum, urine, pleural effusions, cerebro spinal fluid, etc.).

The patient is generally a human, preferably an adult human. In some embodiments, the patient is a diabetes patient, for example a type II diabetes patient on insulin.

Cardiac specific membrane polypeptides may be detected in the patient sample itself, or may be detected in material derived from the sample. These are still considered to be "patient samples" within the meaning of the invention.

Detection methods of the invention can be conducted in vitro or in vivo.

Detecting the Level of a Cardiac Specific Membrane Polypeptide

Various techniques are available for detecting the level of particular polypeptides in a sample. These techniques will usually rely on a detection reagent specific for the cardiac specific membrane polypeptide, i.e. a reagent which will bind preferentially to the target cardiac specific membrane polypeptide.

These techniques include general immunoassay techniques which are based on the specific interaction between an antibody and an antigenic amino acid sequence in the polypeptide. Suitable techniques include standard immunohistological methods, ELISA, RIA, FIA, immunoprecipitation, immunofluorescence, etc.

Where antibodies are used as the detection reagent these may be of any isotype (e.g. IgA, IgG, IgM i.e. an α, γ or μ heavy chain). Antibodies may have a κ or a λ light chain. Within the IgG isotype, antibodies may be IgG1, IgG2, IgG3 or IgG4 subclass. The term "antibody" includes any suitable natural or artificial immunoglobulin or derivative thereof. In general, the antibody will comprise a Fv region which possesses specific antigen binding activity. This includes, but is not limited to: whole immunoglobulins, antigen binding immunoglobulin fragments (e.g. Fv, Fab, F(ab')2 etc.), single chain antibodies (e.g. scFv), oligobodies, chimeric antibodies, humanized antibodies, veneered antibodies, etc.

Antibodies may be polyclonal or monoclonal.

Other detection reagents include aptamers and peptides which bind to the cardiac specific membrane polypeptide.

Cardiac specific membrane polypeptides can also be detected by functional assays e.g. assays to detect binding activity or enzymatic activity. The skilled person will be aware of suitable assays.

Another way of detecting cardiac specific membrane polypeptides is to use standard proteomics techniques e.g.

purify or separate polypeptides and then detect the protein of interest based on size or using immunoaffinity techniques such as Western blots. For example, polypeptides can be separated using SDS PAGE and polypeptide spots can be compared against a protein of corresponding size. The proteins may then be transferred to nitrocellulose or other suitable medium for Western blotting. The proteins may also be detected/sequenced by mass spectroscopy.

Cardiac specific membrane polypeptides can also be detected in vivo. For example, a labelled (e.g. a radioactive or fluorescent label) detection reagent may be injected into a patient and the amount of label determined using a suitable scanner or other device.

In a preferred embodiment the invention the cardiac specific membrane polypeptide will be detected using a "point of care test" (POCT). Such assays are intended to be used for diagnostic testing at or near the site of patient care. POCT are usually transportable, portable, and handheld instruments (e.g., blood glucose meter, nerve conduction study device) and test kits (e.g., CRP, HBA1C, Homocystein, HIV salivary assay, etc.).

A preferred example of a POCT is a membrane-based test strip, optionally enclosed by a plastic test cassette, which comprises a detection reagent which binds specifically to the cardiac specific membrane polypeptide being tested, along with a control. These tests require small amounts of patient sample, for example they can require only a single drop of whole blood, urine or saliva, and can be performed and interpreted by any general physician within minutes.

Major benefits are obtained when the output of a POCT device is made available immediately within an electronic medical record. Results can be shared instantaneously with all members of the medical team through the software interface enhancing communication by decreasing turn around time (TAT). A reduction in morbidity and mortality has been associated with goal-directed therapy (GDT) techniques when used in conjunction with POCT and the electronic medical record.

The term "higher" when referring to the level of cardiac specific membrane protein means a greater level. The invention is based on the discovery that cardiac specific membrane proteins are released from cardiac cells under ischemic conditions and therefore, there will be more of the cardiac specific membrane present in a patient sample if that patient is suffering from a cardiac disorder.

For example, the level of cardiac specific membrane polypeptide is considered to be higher in the patient sample if there is a greater percentage of the polypeptide when compared to the level of the polypeptide in the control sample. Preferably there is greater than 150% of cardiac specific membrane protein in the patient sample compared to the negative control, i.e. at least 200, 300, 500, 750, 1000, 1500, 2000% or more.

The term "detecting the level" also includes situations where there is an absence of the polypeptide to be detected. A sample may contain or be suspected of containing a cardiac specific membrane protein intended for detection. Even if the cardiac specific protein is absent, however, the method is still "for detecting" the cardiac specific membrane protein.

Techniques may require the enrichment of target polypeptides prior to detection and suitable techniques will be apparent to the person skilled in the art.

Controls

As described above, cardiac specific membrane polypeptides are released from cardiac cells into the surrounding environment and thus the patient's blood stream. To detect these polypeptides, a reference point is typically needed i.e. a control. Analysis of the control sample gives a standard level of polypeptide against which a patient sample can be compared. As the presence of cardiac specific membrane polypeptides is negligible under normal conditions and highly elevated in cardiac disorders, however, a reference point may not always be necessary—significant levels indicate a disorder. Even so, the use of controls is preferable, particularly for standardization or for quantitative assays.

A negative control gives a background or basal level of expression against which a patient sample can be compared. Higher levels of cardiac specific membrane polypeptides relative to a negative control indicate that the patient from whom the sample was taken is suffering from a cardiac disorder. Conversely, equivalent levels of cardiac specific membrane polypeptides indicate that the patient does not have a cardiac disorder.

A negative control will generally comprise material from patients who are not suffering from a cardiac disorder. The negative control could be a sample from the same patient as the patient sample, but taken at an earlier stage in the patient's life. Typically, the negative control will be the same tissue as the patient sample being tested (e.g. a blood sample).

In some embodiments, the negative control is from a diabetes patient who does not have an acute cardiac disorder and preferably does not have a cardiac disorder or is from a group of such patients. In some embodiments, the diabetes patient is a type II diabetes patient on insulin.

A positive control gives a level of expression against which a patient sample can be compared. Equivalent or higher levels of cardiac specific membrane polypeptides relative to a positive control indicate that the patient from whom the sample was taken has a cardiac disorder. Conversely, lower levels of cardiac specific membrane polypeptides indicate that the patient does not have a cardiac disorder.

A positive control will generally comprise material from a patient known to have a cardiac disorder.

Although not wishing to be bound by this theory, the inventor proposes that naturally occurring levels of cardiac specific membrane proteins may vary according to the age and ethnicity of the patient. The levels may also very according to the cardiovascular fitness level of patients and fitter patients may have elevated base levels of cardiac specific membrane proteins. In addition, patients who have recently taken part in physical exercise may have elevated levels. Therefore, it may be necessary to match the control sample(s) based on age, ethnicity, cardiovascular fitness and/or time since last physical exercise. Preferably, where the control sample is taken from another patient, that patient will be chosen to match the age and/or ethnicity of the patient being tested.

Other suitable positive and negative controls will be apparent to the skilled person.

Methods for Evaluating the Effectiveness of a Treatment for a Cardiac Disorder

As described above, the methods of the invention are also suitable for monitoring the efficacy of a treatment regimen for the treatment of cardiac disorders.

The method comprises assessing the level of a cardiac specific membrane protein in a patient sample before, during and/or after treatment and comparing said level to a control level.

The level of cardiac specific membrane protein will normally be measured at multiple points throughout the patient's treatment. Preferably the level of a cardiac specific membrane protein will be measured before treatment commences. Preferably the level of a cardiac specific membrane protein will then be measured at one or more time points throughout the course of the patient's treatment. The level of a cardiac specific membrane protein may also be measured after cessation of the treatment.

A reduction in the level of a cardiac specific membrane protein during treatment indicates that the treatment is effective in treating cardiac disorders.

Diagnostic Device

The invention also includes a diagnostic device for use in diagnosing a cardiac disorder, wherein the device permits determination of the level of a cardiac specific membrane polypeptide in a patient sample and comparison of said level to a control level, wherein a level that is higher to said control level is indicative of the disorder.

Preferably the device comprises a detection reagent which is specific for the cardiac specific membrane polypeptide. Preferably the detection reagent is an antibody, aptamer or peptide which preferentially binds to the cardiac specific membrane protein. Alternatively the detection reagent may be a substrate of the cardiac specific membrane protein, which upon interaction with the cardiac specific membrane protein causes a detectable change.

Where antibodies are used as the detection reagent these may be of any isotype (e.g. IgA, IgG, IgM i.e. an $\alpha$, $\gamma$ or $\mu$ heavy chain). Antibodies may have a $\kappa$ or a $\lambda$ light chain. Within the IgG isotype, antibodies may be IgG1, IgG2, IgG3 or IgG4 subclass. The term "antibody" includes any suitable natural or artificial immunoglobulin or derivative thereof. In general, the antibody will comprise a Fv region which possesses specific antigen binding activity. This includes, but is not limited to: whole immunoglobulins, antigen binding immunoglobulin fragments (e.g. Fv, Fab, F(ab')2 etc.), single chain antibodies (e.g. scFv), oligobodies, chimeric antibodies, humanized antibodies, veneered antibodies, etc.

Antibodies may be polyclonal or monoclonal.

Preferably the detection reagent is labelled with a detectable label, e.g. a radioactive or fluorescent label, or a biotin label.

Preferably the device comprises a negative and/or positive control as described above.

In a preferred embodiment the invention the diagnostic device is a "point of care test" (POCT). Such assays are intended to be used for diagnostic testing at or near the site of patient care. The POCT may be a transportable, portable, and handheld instrument or kit.

A preferred example of a POCT is a membrane-based test strip, optionally enclosed by a plastic test cassette, which comprises the detection reagent which binds specifically to the cardiac specific membrane polypeptide being tested, along with a control. These tests require small amounts of patient sample, for example they can require only a single drop of whole blood, urine or saliva, and can be performed and interpreted by any general physician within minutes Preferably the output of the POCT device is made available immediately within an electronic medical record. Results can be shared instantaneously with all members of the medical team through the software interface enhancing communication by decreasing turn around time (TAT). A reduction in morbidity and mortality has been associated with goal-directed therapy (GDT) techniques when used in conjunction with POCT and the electronic medical record.

The diagnostic devices of the invention may also include reagents for the detection of other known biomarkers associated with cardiac disorders, for example, the troponins cTnT and cTnI. the method of the invention can be used in combination with other methods for diagnosing cardiac disorders, for example physical assessment of a patient's symptoms, including electrocardiograms (ECG), as well as other biochemical assays, for example assessment of troponin levels Uses The invention also includes a cardiac specific membrane protein for use in a method of diagnosing a cardiac disorder in a patient, the method comprising detecting the level of a cardiac specific membrane polypeptide in a patient sample and comparing said level to a control level, wherein a level that is higher to said control level is indicative of the disorder.

The invention also includes the use of a cardiac specific membrane protein in the manufacture of a medicament for the diagnosis of a cardiac disorder in a patient.

General

The term "comprising" encompasses "including" as well as "consisting" e.g. a composition "comprising" X may consist exclusively of X or may include something additional e.g. X+Y.

The term "about" in relation to a numerical value x means, for example, $x \pm 10\%$.

The word "substantially" does not exclude "completely" e.g. a composition which is "substantially free" from Y may be completely free from Y. Where necessary, the word "substantially" may be omitted from the definition of the invention.

MODES FOR CARRYING OUT THE INVENTION

EXAMPLE 1

Testing Glut4 Levels

Serum Samples

Figure 1:
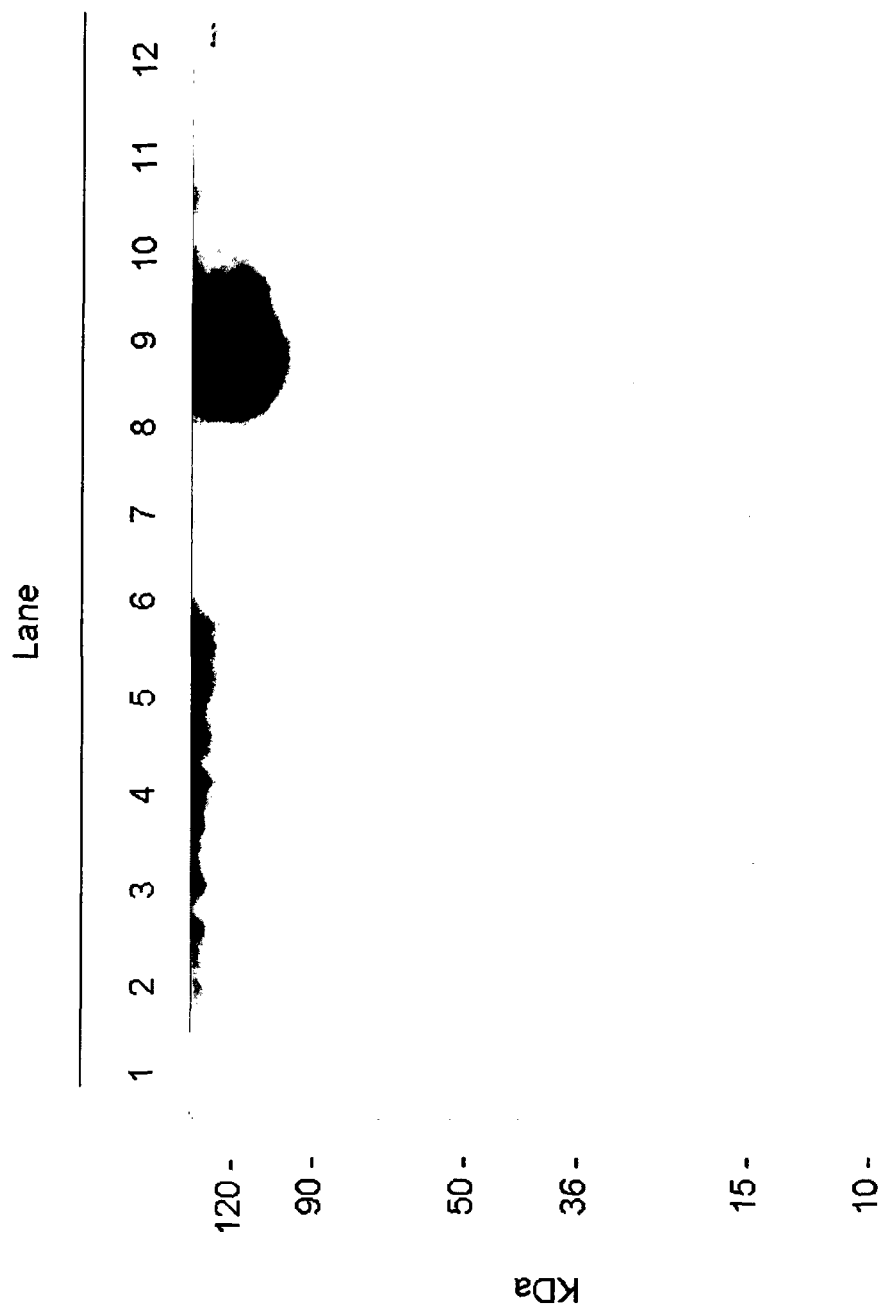
FIG. 1: GLUT-4 Expression in 11 healthy volunteer subjects (Lanes 2-12). All were cTnI negative (<0.02 µg/L) and IMA negative (<85 KU/L). Autoradiograph exposure 2 minutes.

Serum samples were obtained from whole blood drawn in plain Vaccutainer™ serum separator Gel tubes (Beckton Dickenson) from eleven healthy donors. The donors declared no history of prior myocardial infarction, no immediate family history (siblings or parents) of myocardial infarction and no known past history of coronary artery disease.

Redundant serum samples were obtained from whole blood drawn in plain Vaccutainer™ serum separator Gel tubes (Beckton Dickenson) from nine patients who had a final diagnosis of ST segment elevation acute myocardial infarction (STEMI) according to the universal definition of AMI (Circulation 2007; 116:2634-2653).

Redundant serum was obtained from whole blood drawn in plain Vaccutaine™ serum separator Gel tubes (Beckton Dickenson) at timed intervals of 0, 3, 6, 12, 24, 48, 36, 120 and 200 hours from admission from a patient who had a final diagnosis of ST segment elevation acute myocardial infarction (STEMI) according to the universal definition of AMI (Circulation 2007; 116:2634-2653).

Analytical Methods:

All serum samples were tested for cardiac troponin I (cTnI) and Ischemia Modified Albumin (IMA). cTnI was determined using the Centaur TnI-Ultra™ assay (Siemens Healthcare Diagnostics). The total assay imprecision of the assay was 5.3% at 0.08 µg/L and 3.0% at 27.2 µg/L, with a detection limit of 0.006 µg/L and a calibration range of 50 µg/L. The upper $99^{th}$ percentile of a healthy reference population was 0.04 µg/L. IMA was determined using the Albumin Cobalt Binding (ACB®) assay (Inverness Medical) measured specrophotometrically on the Cobas MIRA (Roche Diagnostics). The assay coefficient of variation was 5.09% in the range of 56.67 to 66.57 KU/L and 3.05% in the range 147.17 to 158.03 KU/L. The calibration range was 6 to 125 KU/L. The upper $95^{th}$ percentile of 283 apparently healthy people was 85 KU/L.

Electrophoresis and Western (Immuno) Blotting

Serum proteins were separated using sodium dodecyl sulphate polyacrilamide (12%) Bis-Tris mini-gel electrophoresis (SDS-PAGE) using the Xcell II system (Invitrogen). 10 µL of total protein was loaded onto the gel according to the methods of Läemmli (Läemmli, 1970) and separated for 1 hour at 200V. Separated proteins were then electrophoretically transferred onto nitro-cellulose membranes (Amersham Pharmacia Biotech) using the x-cell II system. The membranes were blocked overnight at 4° C. using 5% non-fat milk powder in PBS. The membranes were then incubated with purified rabbit polyclonal anti-GLUT-4 at a concentration of 2 µg/mL. A 1:1000 donkey anti-rabbit IgG secondary antibody conjugated to horseradish peroxidase (HRP) (Sigma) was added for the detection and were developed using ECL™ chemiluminescent substrate according to the recommended method of the manufacturer (Amersham Pharmacia Biotech). Light emission was detected using autoradiographic film (Kodak) on a compact X2 (x-ograph Ltd).

Figure 5:
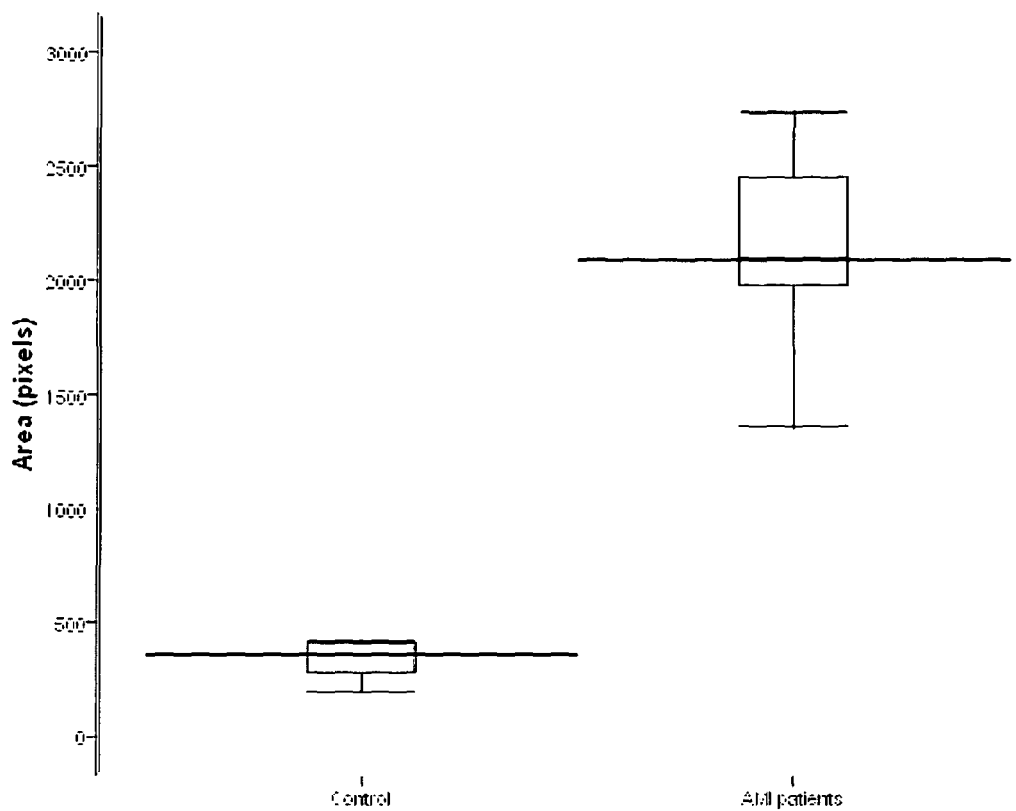
FIG. 5: Quantification of Western Blots. Comparison of control group band intensity to AMI patient group band intensity. Using the medians test, there was a statistically significant difference in the area of the control group bands (median (95% confidence interval)=392pixcel, 95% CI=1964 to 2516) vs. AMI group (median 2092pixel, 95% CI=196 to 1318), p=0.0014.

Using Image-J software, the Western Blot images (jpeg files) are converted to 8-bit to change to greyscale. Background is subtracted by using a rolling ball radius of 50. The image is inverted and using the freehand selection tool a line is drawn around the band. The measurement is given as intensity of pixels within the band. Data are transferred to Microsoft excel and formally compared by the Medians test using Analyse-it add in for Excel. The box and whisker plot was generated using IBM SPSS software version 16.0. Results from the Western blot images are thus presented as FIG. 5 in a box and whisker plot.

Results

Figure 2:
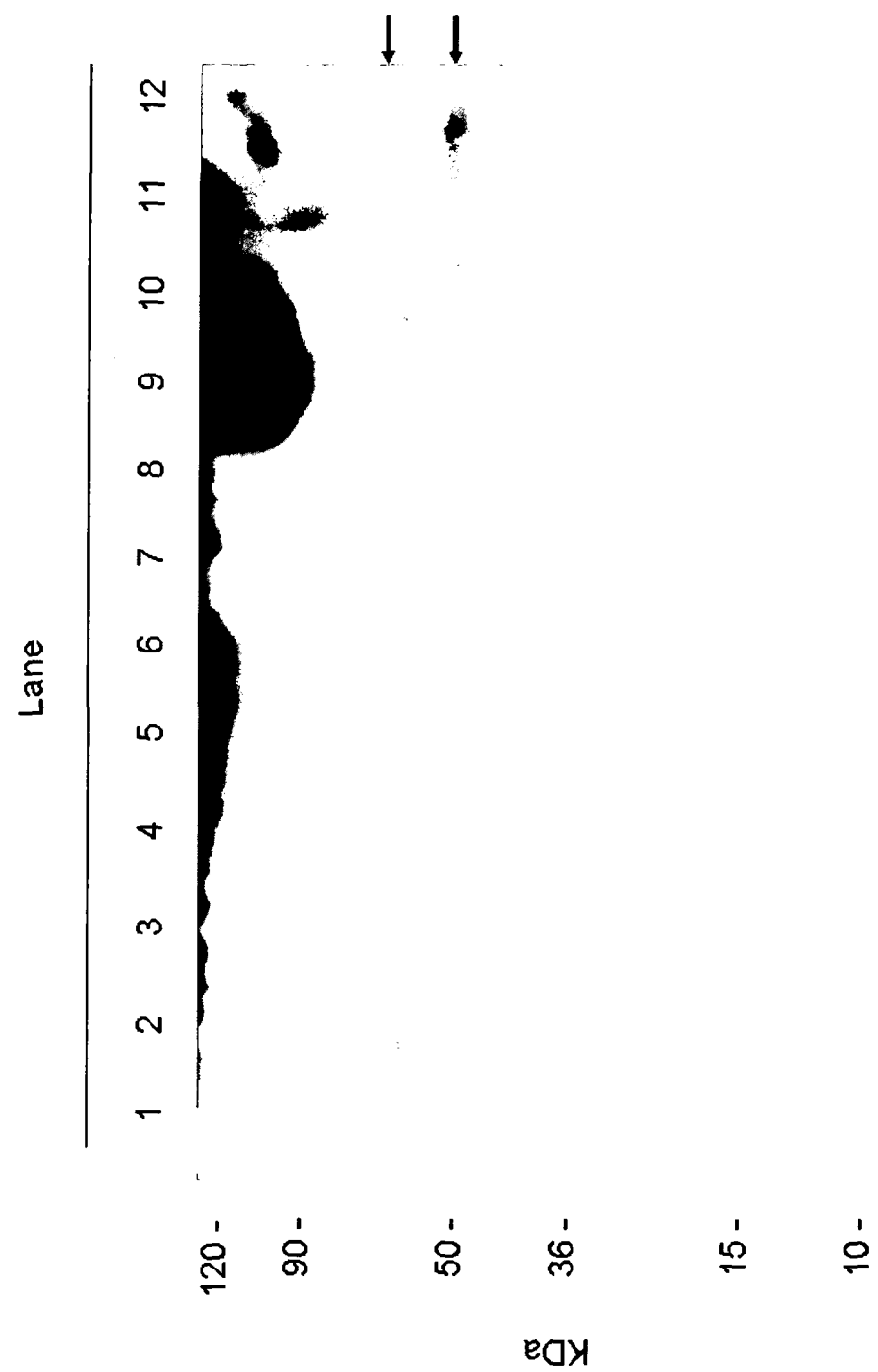
FIG. 2: GLUT-4 Expression in 11 healthy volunteer subjects (Lanes 2-12). All were cTnI negative (<0.02 µg/L) and IMA negative (<85 KU/L). Autoradiograph exposure 5 minutes.
Figure 3:
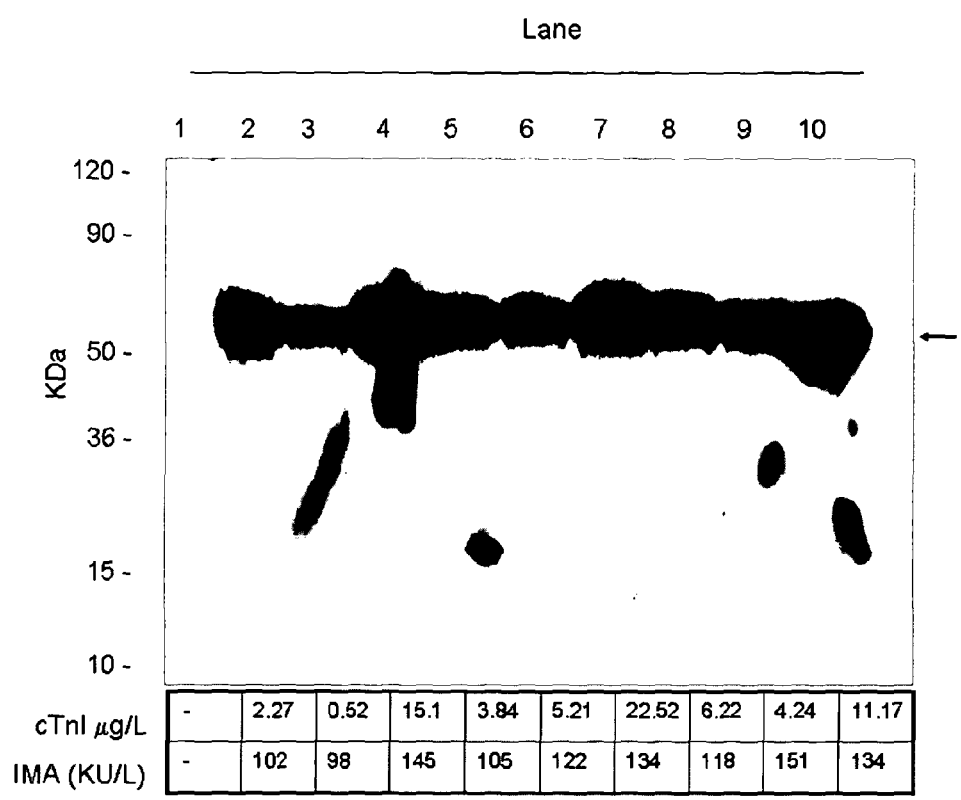
FIG. 3: GLUT-4 Expression in 9 patients (lanes 2-10) presenting with ST-segment elevation myocardial infarction (STEMI). All were cTnI positive (>0.04 µg/L, range 0.52-22.52 µg/L) and IMA positive (>85 KU/L, range 98-151 KU/L). Autoradiograph exposure 5 minutes.
Figure 4:
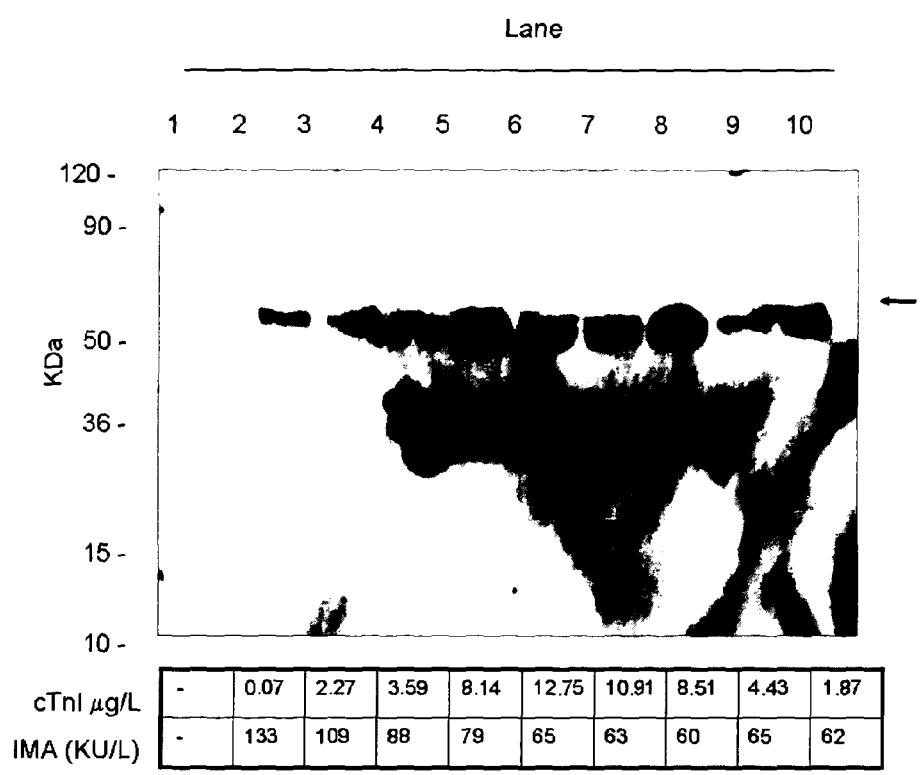
FIG. 4: Kinetic sequence of GLUT-4 expression at timed intervals of 0 hr (lane 2), 3 hr (lane 3), 6 hr (lane 4), 12 hr (lane 5), 24 hr (lane 6), 48 hr (lane 7), 36 hr (lane 8), 120 hr (lane 9) and 200 hr (lane 10) from admission in a patient with a final diagnosis of ST segment elevation myocardial infarction (STEMI). Corresponding cTnI and IMA concentrations are shown in the table below the Western blots.

All serum from healthy volunteers were deemed negative for both cTnI and IMA as all values were below the upper limit of normal stated by the manufacturer. Serum samples were immunoblotted for the presence of GLUT-4. After autoradiographic exposure for two minutes, no bands corresponding to the molecular weight of GLUT-4 were detectable (FIG. 1). At 5 minutes exposure, some healthy subjects (lanes 4,5, 7,8,9,10,12 demonstrated faint bands (FIG. 2) corresponding to approximately 50 KDa. In contrast, heavier bands were demonstrated (FIG. 3) in all subjects with a final diagnosis of STEMI. All STEMI patients were positive for cTnI (range 0.52-22.52 µg/L) and IMA (98-151 KU/L) respectively. A kinetic profile of GLUT-4 was determined by sequentially sampling an STEMI patient at regular time intervals from admission to 200 hrs post admission (FIG. 4). These data demonstrate a change in band intensity and therefore a change in GLUT-4 concentration over the time course of sampling.

Discussion

Serum samples from healthy volunteers have shown the presence of a low background circulating concentration of GLUT-4. In patients who present to the Emergency Room with chest pain and subsequently diagnosed with ST segment myocardial infarction, GLUT-4 concentrations observed in serum are significantly higher. A kinetic profile has been demonstrated in a patient over time showing the fluctuation in GLUT-4 concentration in serum.

EXAMPLE 2

Clinical and Control Patient Sample Groups Tested Via ELISA a) Control Populations a-i) Apparently healthy individuals without an acute cardiac disorder.

The control group will serve to determine the background concentration of the marker in the general population without a known cardiac disorder. Serum has been obtained from subjects >45 years old, randomly selected from the practice lists of seven representative local community practices: 1392 general population subjects were invited to participate. Details of the subjects were collected by questionnaire. Heart rate and blood pressure measurement (the average of two readings), spirometry, electrocardiography (ECG) and echocardiography were performed. Left ventricular ejection fraction (LVEF) was calculated quantitatively using Simpson's apical biplane method taking the average of three readings. Borderline or worse left ventricular systolic dysfunction (LVSD) was defined as LVEF <50%. LV mass was calculated using the Devereux-modified American Society of Echocardiography equation, with left ventricular hypertrophy (LVH) defined as LV mass index >134 g/m2 for men and >110 g/m2 for women. Normal subjects were defined as all attending general population subjects with no history of vascular disease, diabetes mellitus, hypertension, or heavy alcohol intake and receiving no cardiac medication; whose blood pressure was <160/190 mmHg as the mean of two readings; whose fasting blood glucose was <6 mmol/l, whose estimated creatinine clearance (calculated by the diet modification of renal disease equation corrected to a reference creatinine method) was >60 mL/min/1.73 m2; and who had no significant valvular heart disease, LVH, DHF, LVEF <50% or regional wall motion abnormalities on echocardiography.

This population is a very well characterised group of subjects screened for biochemical and physiological parameters to exclude any overt signs of a cardiac disorder. It is very rare to obtain such a selected population especially with supporting echocardiographic data showing normalisation of heart function.

a-ii) Non-acute cardiac disorder diabetic patients.

The cardiac marker cellular location is modified by the action of insulin. Diabetes is a risk factor for the development of heart disease. This population will serve as a specific control group to investigate any correlation between diabetes and/or age with marker expression. Fifty known diabetic patients with either type I (insulin dependent diabetes mellitus, NIDDM) or type II (non insulin dependent diabetes mellitus, IDDM).

The incidence of cardiac troponin positive concentrations outside the remit of acute myocardial infarction (AMI) are now being understood. Troponin is a marker of cardiac cell damage not AMI which remains a clinical diagnosis. With sensitive assays we are now able to detect concentrations cTn in subjects previously deemed normal with less sensitive cTn assays. Diabetics are at particular risk of cardiovascular disease and subsequent development of AMI. Insulin may modulate GLUT 4 translocation to the cell surface membrane so therefore type II diabetic patients on insulin are an important patient group to monitor for GLUT4.

b) Clinical Groups b-i) Acute myocardial infarction (AMI) patients.

The patient population to be tested will cover various age groups with information on clinical history. At least 30 patients will be tested. It is proposed to test the biomarker from a series of samples taken over a period of time.

b-ii) Patients with stable angina have ongoing cardiac ischemia. The severity of the cardiac insult is less than in an acute coronary syndrome.

b-iii) Subjects who initially present with chest pain who do not demonstrate a significant release of cardiac troponin who then convert whilst in the Emergency Room to positive for cardiac troponin. This population is rarely seen.

Sample Analysis:

Enzyme linked immunosorbent assay (ELISA) using plates from Uscn Life Science Inc., Wuhan, China.

Sequence Listing

```
Glut4
                                                                SEQ ID NO: 1
  1 MPSGFQQIGS EDGEPPQQRV TGTLVLAVFS AVLGSLQFGY NIGVINAPQK VIEQSYNETW

61 LGRQGPEGPS SIPPGTLTTL WALSVAIFSV GGMISSFLIG IISQWLGRKR AMLVNNVLAV

121 LGGSLMGLAN AAASYEMLIL GRFLIGAYSG LTSGLVPMYV GEIAPTHLRG ALGTLNQLAI

181 VIGILIAQVL GLESLLGTAS LWPLLLGLTV LPALLQLVLL PFCPESPRYL YIIQNLEGPA

241 RKSLKRLTGW ADVSGVLAEL KDEKRKLERE RPLSLLQLLG SRTHRQPLII AVVLQLSQQL

301 SGINAVFYYS TSIFETAGVG QPAYATIGAG VVNTVFTLVS VLLVERAGRR TLHLLGLAGM

361 CGCAILMTVA LLLLERVPAM SYVSIVAIFG FVAFFEIGPG PIPWFIVAEL FSQGPRPAAM

421 AVAGFSNWTS NFIIGMGFQY VAEAMGPYVF LLFAVLLLGF FIFTFLRVPE TRGRTFDQIS

481 AAFHRTPSLL EQEVKPSTEL EYLGPDEND
```

REFERENCES

Davies M J, Thomas A C, Knapman P A, Hangartner J R. Circulation 1986; 73: 418-427.

Falk E: Circulation 1985; 71: 699-708

Thygesen K, et al., Circulation. 2007, 116:2634-53.

Gaze D C, J Med Biochem 2010, 29(4): 1-5

Keller T, Zeller T, Peetz D, Tzikas S, Roth A, Czyz E, et al. N Engl J Med 2009; 361: 868-77.

Reichlin T, Hochholzer W, Bassetti S, Steuer S, Stelzig C, Hartwiger S, et al. N Engl J Med 2009; 361: 858-67.

The invention claimed is:

1. A method of diagnosing myocardial infarction in a patient, comprising:
   (a) obtaining a serum sample or plasma sample from a blood sample from the patient;
   (b) detecting with an antibody the level of Glut4 in the serum sample or plasma sample from the patient;
   (c) comparing the Glut4 level in the serum sample or plasma sample to a control Glut4 level that is a standard level in serum or plasma in patients who are not suffering from any cardiac disorder; and
   (d) diagnosing the patient with myocardial infarction if the Glut4 level in the serum sample or plasma sample is statistically significantly higher than the control Glut4 level,
   wherein the antibody specifically binds Glut4 and wherein Glut4 consists of SEQ ID NO: 1.

2. The method of claim 1, wherein the antibody is labelled.

3. The method of claim 1, wherein the detection is carried out using an ELISA, RIA or an immunofluorescence assay.

4. The method of claim 1, further comprising treating the patient diagnosed in step (d) for myocardial infarction, wherein the level of Glut4 in the patient sample is detected before, during and/or after treatment for myocardial infarction.

5. The method of claim 4, wherein the antibody is labelled.

6. The method of claim 4, wherein the detection is carried out using an ELISA, RIA or an immunofluorescence assay.

* * * * *